United States Patent [19]

Nabity et al.

[11] Patent Number: 5,701,646

[45] Date of Patent: Dec. 30, 1997

[54] METHOD OF MAKING A SENSOR

[75] Inventors: Frederick Alan Nabity, Lincoln; Paul George Wright, Pleasant Dale; Raymond Hulinsky; Douglas Timothy Carson, both of Lincoln, all of Nebr.

[73] Assignee: Isco, Inc., Lincoln, Nebr.

[21] Appl. No.: 564,793

[22] Filed: Nov. 29, 1995

Related U.S. Application Data

[62] Division of Ser. No. 430,155, Apr. 26, 1995, which is a division of Ser. No. 807,200, Dec. 16, 1991, Pat. No. 5,401,139, which is a division of Ser. No. 474,154, Feb. 2, 1990, Pat. No. 5,125,801.

[51] Int. Cl.[6] ................................................. H01L 41/22
[52] U.S. Cl. ...................... 29/25.35; 310/338; 310/800
[58] Field of Search .......................... 29/25.35; 310/800, 310/338, 339

[56] References Cited

U.S. PATENT DOCUMENTS

| 4,216,403 | 8/1980 | Krempl et al. | 310/338 |
| 4,304,126 | 12/1981 | Yelke | 310/338 |
| 4,391,147 | 7/1983 | Krempl et al. | 310/338 |

Primary Examiner—Carl E. Hall
Attorney, Agent, or Firm—Vincent L. Carney

[57] ABSTRACT

A method of making a sensor wherein flexible conduit means is assembled with a fixture having a strain-sensitive film and electrical connections are made to the film whereby variations in fluid pressure in the conduit means can be detected.

13 Claims, 9 Drawing Sheets

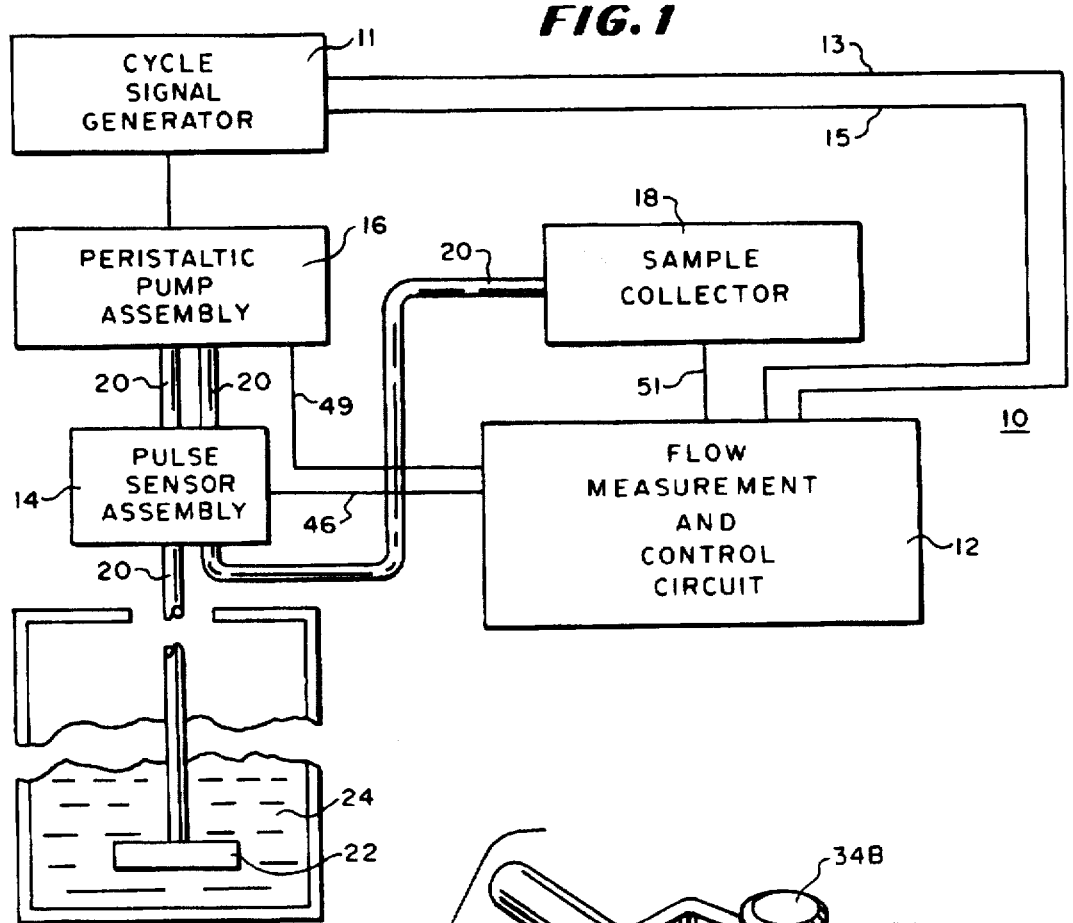
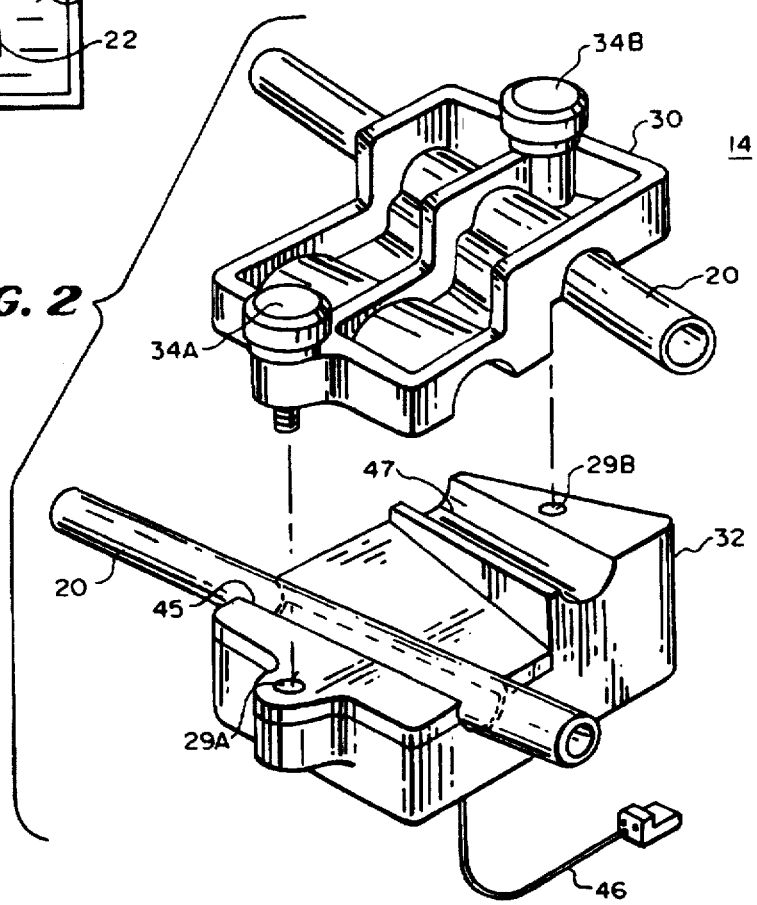

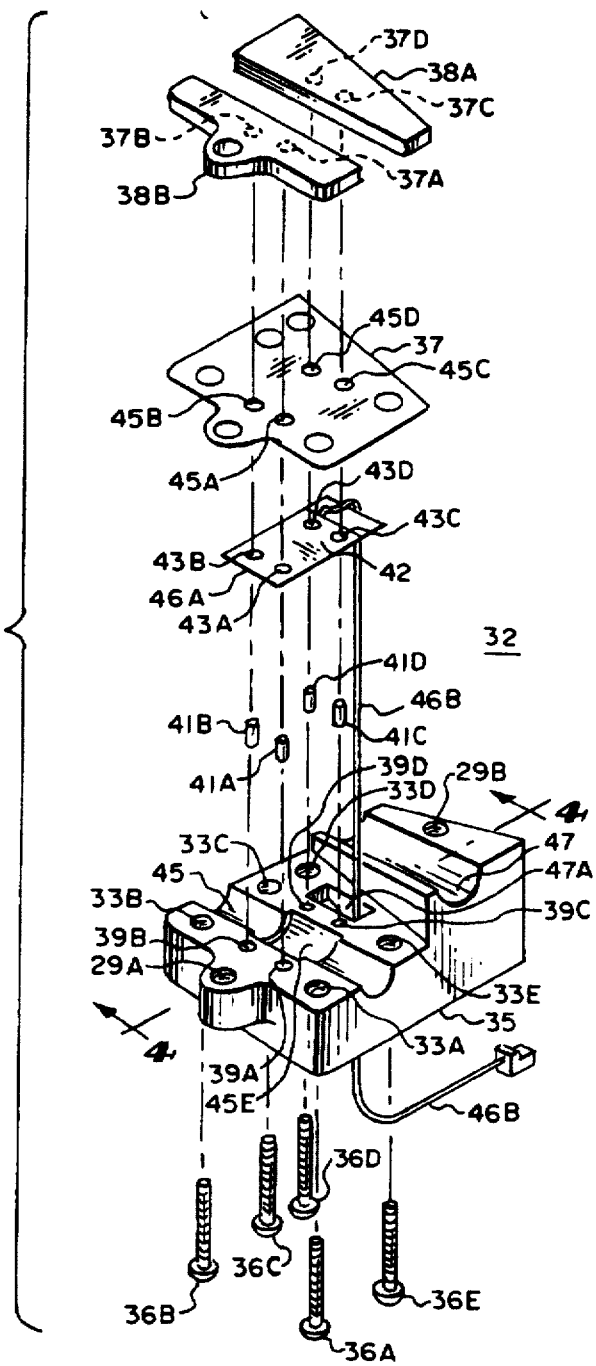
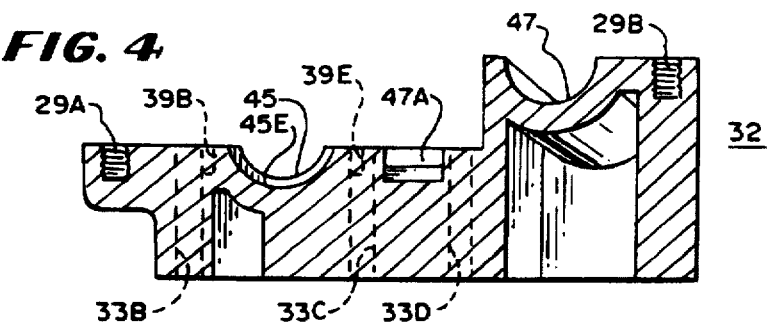

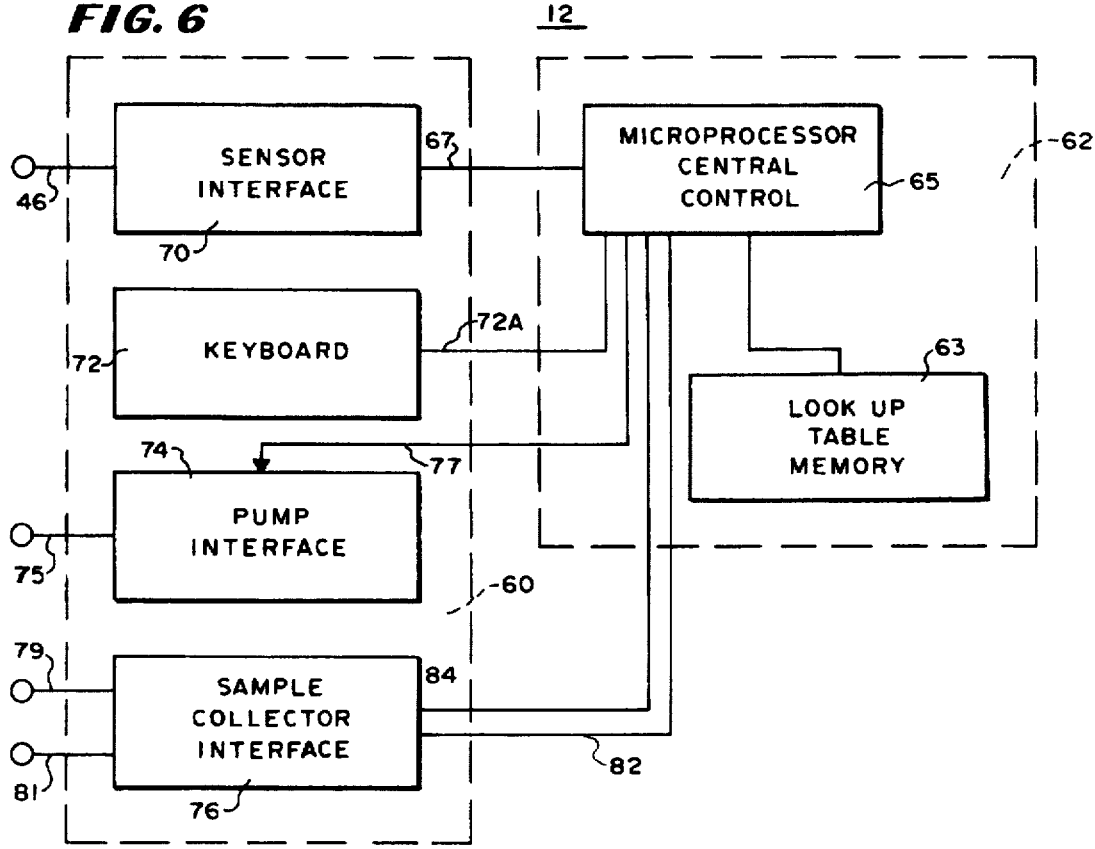
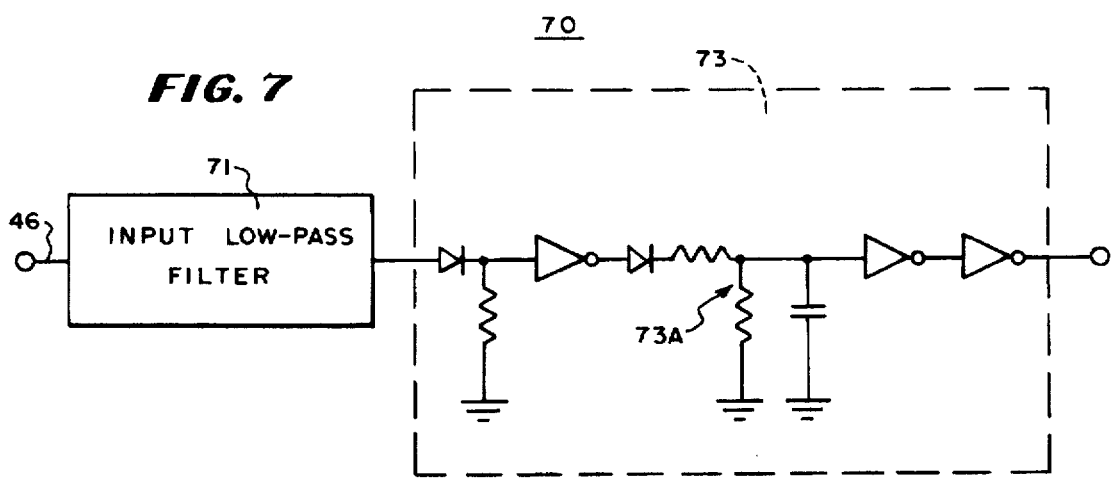

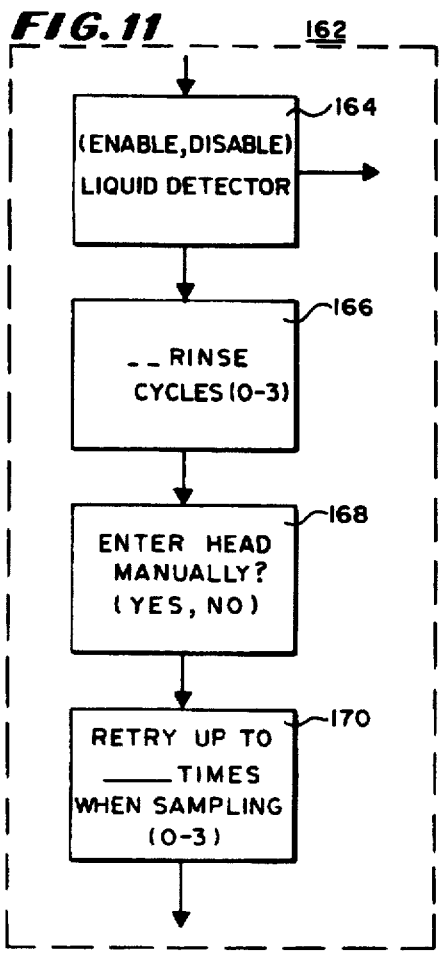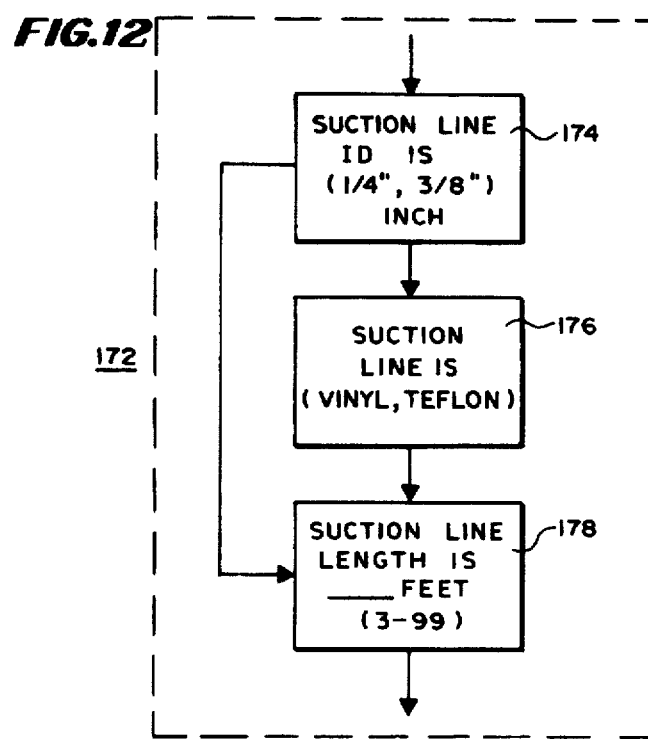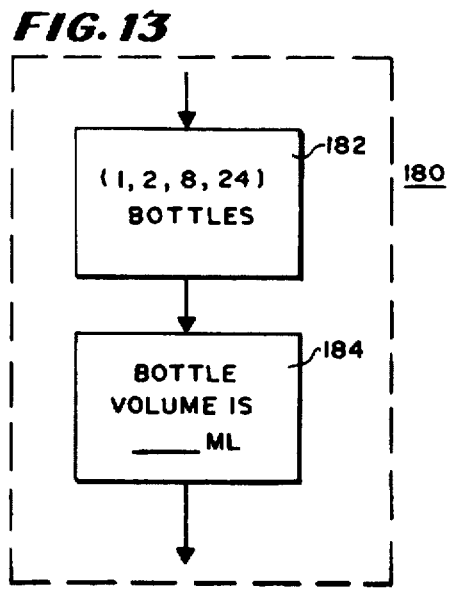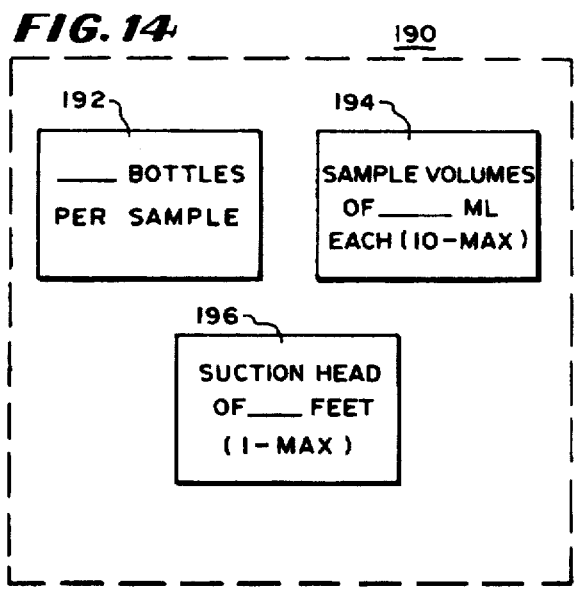

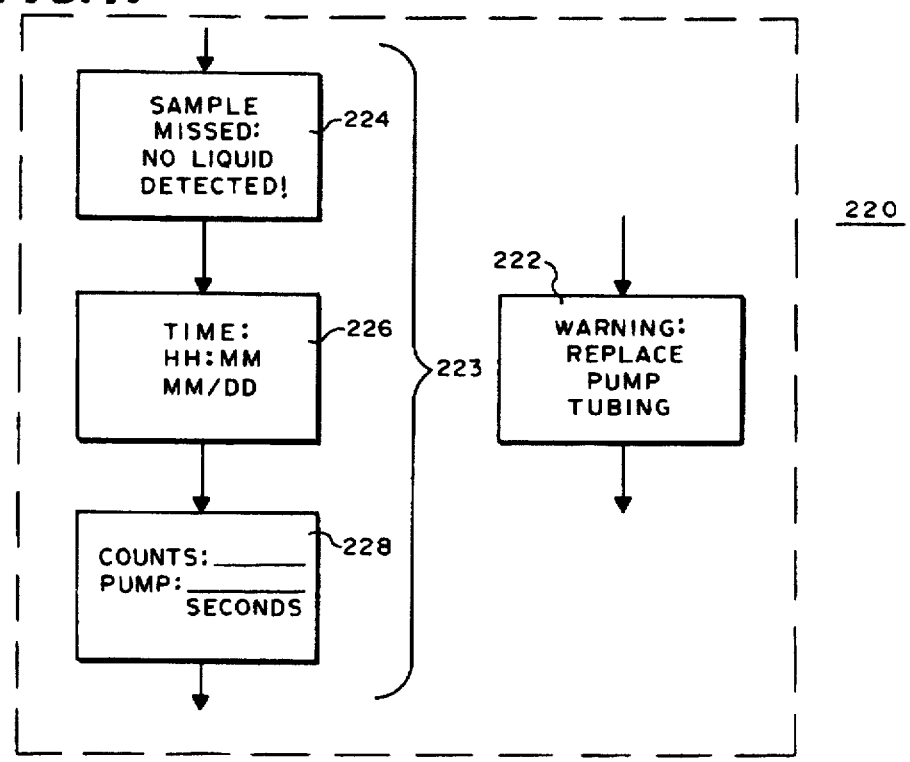
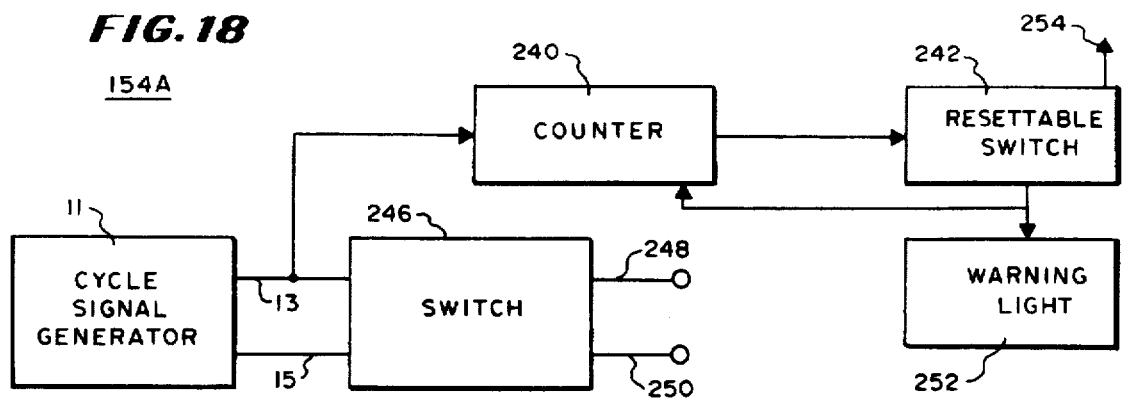

METHOD OF MAKING A SENSOR

RELATED CASES

This application is a division of application Ser. No. 08/430,155, filed Apr. 26, 1995, which is a divisional application of U.S. application Ser. No. 07/807,200, filed Dec. 16, 1991, now U.S. Pat. No. 5,401,139 which is a divisional of U.S. application Ser. No. 07/474,154 filed Feb. 2, 1990, now U.S. Pat. No. 5,125,801 in the names of Frederick Alan Nabity, Paul George Wright, Raymond Hulinsky and Douglas Timothy Carson for PUMPING SYSTEM and assigned to the same assignee as this application.

BACKGROUND OF THE INVENTION

This invention relates to pumping systems and more particularly to pumping systems that utilize a pulsating pump to draw samples from a source of liquid.

It is known to pump liquids from a liquid source through a pulsating pump, such as for example a peristaltic pump, from U.S. Pat. No. 4,415,011 to Douglas M. Grant, issued Nov. 15, 1983, and from U.S. Pat. No. 4,660,607 to Carl D. Griffith, issued Apr. 28, 1987. In such a process, the water interface in the conduit through which the liquid is being pumped is sensed to provide an indication of where the liquid is in the conduit.

Several different sensing mechanisms have been utilized in such pumps such as an optical sensing mechanism, a capacitance sensing mechanism and a electrical conductivity sensing mechanism. The information about the sensed interface is utilized together with other information to meter a fixed volume of liquid into one or more sample containers. U.S. Pat. No. 4,415,011 discloses the metering of liquid by counting cycles of the pump from the shaft of the pump.

In the prior art apparatus, the sensors are either internal or external to the conduit and utilize several different arrangements such as by sensing a change in capacitance between two electrodes outside the conduit as the liquid interface passes through or by sensing changes in the absorption of light transmitted through the conduit or changes in electrical conductivity.

These prior art pumps and sensing mechanisms have several disadvantages such as for example: (1) under some circumstances, the sensing mechanism may have difficulty in distinguishing between a continuous flow of the liquid and spurts of liquid that may be splashed through the sensing point; (2) the pump may slow due to battery drain or other unexpected effects; (3) the head of water may suddenly change, causing variations in pumping; or (4) conductivity and capacitive sensors are prone to malfunctions caused by bridges and changes in the conductivity of liquids.

SUMMARY OF THE INVENTION

Accordingly, it is an object of the invention to provide a novel pumping system.

It is a further object of the invention to provide a pumping system which senses the location of liquid being pumped in a conduit by changes in force caused by the pumping.

It is a still further object of the invention to provide a pumping technique which is controlled in accordance with pulses caused by a pulsating pump.

It is a still further object of the invention to provide a pumping system which utilizes stored statistical data along with other information relating to the head of pressure and size of conduits to measure the amount of liquid being pumped.

It is a still further object of the invention to provide a novel pumping technique in which a combination of measurements of cycles of the pump and stored data is used to meter the amount of liquid being pumped.

It is a still further object of the invention to provide a novel pumping technique for metering the amount of liquid being pumped by stored statistical data relating the cycles of the pump to pressure head and flow of liquid, and other information such as that relating to conduit size and the like.

It is still another object of the invention to provide a liquid metering pump that uses detected pump cycles and stored data including conduit size, and pressure head to correlate detected pump cycles with volume of liquid pumped.

In accordance with the above and further objects of the invention, a pumping system includes: (1) a pump that creates pressure pulses as it pumps; (2) a conduit through which liquid is drawn; (3) a sample container; and (4) a sensor for sensing pulses in the conduit. The sensor is positioned at a location along the conduit where it generates a signal related to pressure or force in the conduit. In the preferred embodiment, it is a piezoelectric film which senses motion of the conduit as it attempts to expand because of force generated by the pump such as the back pressure in the liquid caused by reaction to backed inertia of moving water when a pump roller closes the conduit against further flow.

In the operation of the sensor, the sensor generates electrical signals indicating pulses caused by the pump. Signals generated at the time that the liquid reaches a predetermined point are distinguished from other pulsations to indicate the interface of the liquid. Pulses are counted and when there are interruptions in the count, a standard criteria is applied to determine if the interruption is because the initial indication of an interface of liquid was false and only caused by splashing or surging or the like or whether it was a genuine interface and the lapse in pulses was an error. Pulses are added which indicate that the liquid is indeed flowing beyond a predetermined point.

To determine when a predetermined amount of liquid has been deposited in a container, the length of conduit, inner diameter of conduit and the like are measured, and in the preferred embodiment, entered into the memory of a microprocessor. A statistical base determined over a number of runs is utilized so that when the interface of the liquid is detected, the number of counts of the pump motor before the interface reaches a predetermined location is used as an indication of the head of water pressure by statistically relating it in a look-up table.

The head of pressure is then utilized together with the known length from the interface to the sample collector to determine how many cycles of a pump are required to meter approximately the right amount of liquid into the container in the sample collector. The number of cycles is determined from a statistical base in a look-up table which is corrected for the characteristics that affect pulse counts such as drag, head of pressure, cross-sectional area of conduit, length of conduit, or the like.

When the preset volume of liquid as determined by the number of pumping cycles has been deposited in the container, the pump reverses direction to purge the tube and prevent further liquid from being deposited into the container. This cycle may be repeated manually or automatically under the control of a microprocessor with alternate purge and filling cycles in a manner long used in the art.

With the liquid sensor, rinse cycles can be performed in which the liquid can be drawn to a more precise point than in prior art apparatus so as to better clean the conduit. With this combination, a rinse may encompass a large portion of the conduit without causing liquid to flow into a sample container. The rinse liquid can be drawn even to the highest point in the conduit downstream of the pump with safety but in the preferred embodiment it is stopped at the inlet of the pump.

In the preferred embodiment, the interface of the liquid is determined by a change of measured amplitude in the pulses generated by the strain sensitive piezoelectric film. This change in amplitude occurs if the sensor is positioned on the inlet side of the pump when the liquid approaches the pump. Force pulses are created by: (1) inertia because of changes in momentum from blocking the liquid by closure of the conduit in which liquid is flowing by a roller; and (2) other forces such as roller pressure transmitted through the liquid or tube wall. It occurs at a point because there is a cushion of air between the sensor and the pump that attenuates the pulse. If the sensor is located on the outlet side of the pump, the change in amplitude occurs when the liquid reaches the sensor.

In the preferred embodiment, once the pumping system has determined that liquid is flowing from the amplitude of measured pulses, sensed cycles of the pump are counted during the time the amplitude of the strain pulses is above the threshold.

From the above description, it can be understood that the pumping system of this invention has several advantages, such as for example: (1) it more precisely meters the amount of liquid because it is based on pulsations and pump cycles and reacts to the head of pressure; (2) measurement is made using a criteria which is not altered by splashing or surging of the water or the light transmission characteristics of an optical path or the capacitance or other noise effects that has caused difficulties with other types of sensors; and (3) the metering criteria is partly determined by a statistical base to compensate more readily for unpredicted variations between samples; and (4) the sensor is not wetted by the pumped liquid.

SUMMARY OF THE DRAWINGS

The above noted and other features of the invention will be better understood from the following detailed description when considered with reference to the accompanying drawings, in which:

FIG. 1 is a block diagram of a pumping system in accordance with the invention;

FIG. 2 is a partially exploded, perspective view of a liquid sensing device used in the embodiment of the invention shown in FIG. 1;

FIG. 3 is an exploded perspective view of a liquid sensing device used in the embodiment the invention shown in FIG. 1;

FIG. 4 is an elevational sectional view of a portion of a liquid sensing device used in the embodiment of the invention shown in FIG. 3;

FIG. 6 is a block diagram of a portion of the pumping system of FIG. 1;

FIG. 7 is a block diagram illustrating a process used in the pumping system of FIG. 1;

FIG. 11 is a flow diagram of another portion of the embodiment of FIG. 9;

FIG. 12 is a flow diagram of still another portion of the embodiment of FIG. 9;

FIG. 13 is a block diagram of still another portion of the embodiment of FIG. 9;

FIG. 14 is a block diagram of another portion of the program of FIG. 8;

FIG. 17 is a block diagram of still another portion of the embodiment of FIG. 8; and FIG. 18 is a block diagram of another embodiment of FIG. 10.

DETAILED DESCRIPTION

Figure 5:
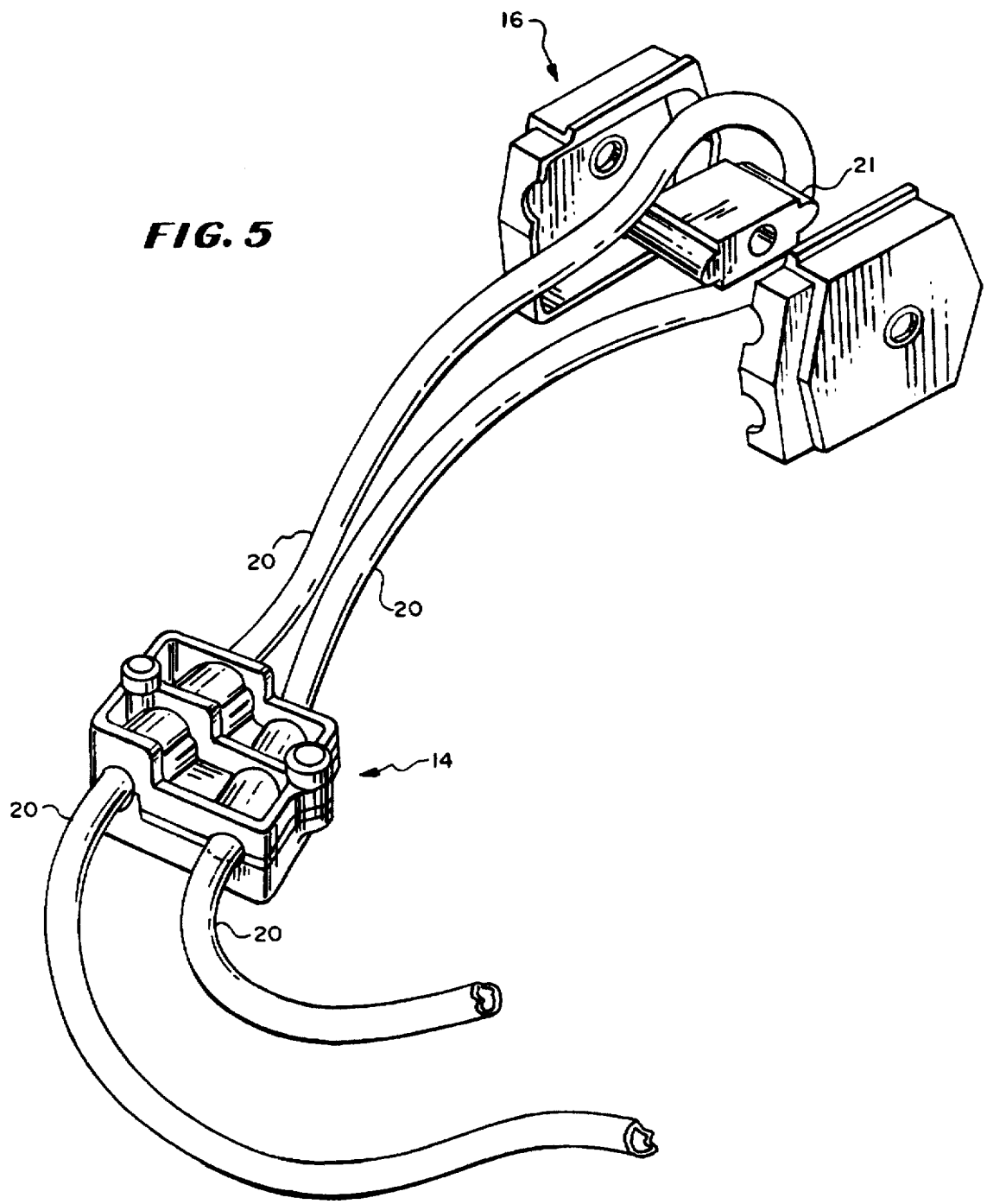
FIG. 5 is a fragmentary, exploded perspective view of the liquid sensing device and pumping system used in the embodiment of the invention shown in FIG. 1.

In FIG. 1, there is shown a block diagram of a pumping system 10 having a flow measurement and control circuit 12, a pulse sensor assembly 14, a peristaltic pump 16, a cycle signal generator 11 for generating signals indicating the cycles of the pump, a sample collector 18 and a conduit 20. The conduit 20 is fastened to and communicates with an inlet straining device 22 and extends through the pulse sensor assembly 14, the peristaltic pump assembly 16 and the sample collector 18 into which it supplies liquid.

The flow measurement and control circuit 12 is electrically connected to the pulse sensor assembly 14 to receive signals therefrom indicating pumping cycles of liquid after the liquid has reached a specific location and to control the peristaltic pump assembly 16 and sample collector 18 to deposit predetermined volumes of liquid into a sample container or a group of sample containers in accordance with a preprogrammed procedure or under the manual control of an operator.

The cycle signal generator 11 is connected to the rotor of the peristaltic pump in the peristaltic pump assembly 16 and generates a predetermined number of pulses for each cycle. These pulses are transmitted to the flow measurement and control circuit 12 through a conductor 13 to provide an indication of pump cycles and through conductor 15 to indicate the direction of rotation (necessary only in one embodiment) for use in controlling the peristaltic pump assembly 16 in a manner to be described hereinafter.

The conduit 20, inlet strainer 22, peristaltic pump assembly 16 and sample collector 18 may be of any suitable type. A similar arrangement is disclosed in U.S. Pat. No. 4,415,011 except that the sample collecting arrangement of U.S. Pat. No. 4,415,011 utilizes a different type of pulse sensor and relies for control of the volume of liquid on a different circuit arrangement and program. Nonetheless, many different control circuits and different types of pumps which produce pulses when they are pumping, types of sample collector 18, inlet strainer 22 or conduit 20 may be used in the invention.

In use, the inlet strainer 22 is inserted in the liquid 24, samples of which are to be drawn and data such as the amount of fluid for each sample, the time between samples, the size of the conduit 20 and the like are entered through a keyboard. The peristaltic pump assembly 16 is started under the control of the flow measurement and control circuit 12 and begins pumping liquid. As it pumps liquid, there is some force applied to the flexible conduit 20 as the liquid 24 begins to move upwardly through the pulse sensor assembly 14 into the peristaltic pump assembly 16.

The pulse sensor assembly 14 senses pulses, and for this purpose is, in the preferred embodiment, a piezoelectric film contacting the conduit to sense expansion of the conduit. A suitable type of film is available from the Kynar Piezo Film Sensor Division of Pennwalt Corporation having an office at 950 Forage Avenue, Norristown, Pa. 19403. This film is described in a booklet entitled "Piezoelectric Film Sensors An Introduction to the Techology", by Douglas Kehrhahn, available from Pennwalt Corporation, Piezo Film Sensor Division, P.O. Box 799, Valley Forge, Pa. 19482.

Because the pulsations from the peristaltic pump assembly 16 are absorbed by air in the conduit 20 until the liquid reaches the peristaltic pump assembly 16, the pulses received by the pulse sensor assembly 14 do not cross a predetermined amplitude threshold until the liquid reaches a predetermined location. This predetermined location depends on the size of the head and the amount of the liquid being pumped. The greater the head, the closer the predetermined location is to the pump. It is possible to locate the sensor directly at the pump or after (downstream of) the pump and this will change the location of the predetermined point. Data in the lookup table must be adapted to this change in location of the sensor.

With this arrangement, the pulse sensor assembly 14 senses pulse amplitude and determines the interface of pulses and applies the signal to the flow measurement and control circuit 12 indicating that the liquid has reached the predetermined location between the peristaltic pump assembly 16 and the sample collector 18. At this point in time, the flow measurement and control circuit 12 may, in accordance with some standard programs, purge the conduit and redraw the fluid 24, or in others, continue to pump to draw a sample and deposit the sample into a container.

When the location of the fluid 24 reaches the sensor after a purge cycle if there is one, the flow measurement and control circuit 12 causes a predetermined amount of fluid to be deposited in a container within the sample collector 18, and in some embodiments, the sample collector may include a distributor or may move containers to deposit sample in succession during different pumping cycles. The number of pumping cycles required is determined in the preferred embodiment by a computer look-up table containing data based on trial and error measurements with conduits of the same inner diameter to determine the number of pumping cycles required for a given volume once the interface has been sensed in a manner to be described in greater detail hereinafter.

The statistical database and look-up tables can be calibrated and continuously updated by standard adaptive techniques. More specifically, the amount of sample deposited in containers can be measured and entered into the database to update the look-up table by providing a better average base for the variable parameters.

The sensor may sense some initial bursts of liquid prior to a constant continuous flow. This happens because the sensor detects an initial flow of liquid but in some circumstances, the fluid 24 drops away from the pump and has to be pulled back to the pump. The fluid measurement and control circuit 12 counts the number of cycles of the pump as indicated by the cycle signal generator 11 for the liquid that flows through a predetermined point and adds those cycles that are significant to the total liquid pumped into a sample container or to a predetermined point required for a rinse or purge cycle.

The counting occurs after the liquid interface reaches the predetermined point. This permits the pumping system to more precisely meter liquid into a container.

In FIG. 2, there is shown a partly exploded perspective view of the pulse sensor assembly 14 having first and second sections 30 and 32. The first and second sections 30 and 32 fit together to form an enclosure having two cylindrical openings extending through it, each of which receive and confine a different part of a length of conduit 20.

One part of the length of the conduit 20 fits in a first groove 45 which receives the conduit 20, with a piezoelectric sensor (not shown in FIG. 2) fitting over it to be strained as the conduit 20 deforms. The conduit 20 is looped through the pump and passes in the other direction through a second cylindrical groove. The two sections are held together by fasteners 34A, 34B In FIG. 3, there is shown an exploded perspective view of the second section 32 having a housing 35, a piezoelectric sensor 42, a woven fiberglass protective member 37 and first and second pin seating inserts 38A and 38B. The housing 35 of the second section 32 receives the protective member 37, piezoelectric sensor 42, and inserts 38A and 38B and forms a unit fastened together with first section 30 to hold the conduit 20 (FIGS. 1 and 2) against motion caused by the pump 16 (FIG. 1) during its rotation against the conduit 20 and to hold and protect the piezoelectric sensor 42 against the conduit to sense changes in pressure within it caused by action of the pump.

The housing 35 includes: (1) five apertures 33A, 33B, 33C, 33D and 33E sized to receive one end of five fasteners 36A, 36B, 36C, 36D and 36E; (2) four smaller apertures 39A, 39B, 39C and 39D which receive one end of four pins 41A, 41B, 41C and 41D that pass through apertures 43A, 43B, 43C and 43D in the piezoelectric sensor 42, and form a part of the holding means for the sensor 42; (3) cylindrical grooves 45 and 47 and a sensing aperture 47A through which the conductor 46B passes. With this arrangement, the housing 35 aids in holding the sensor 42, the protective member 37 and the inserts 38A and 38B in place. The first section 30 and second section 32 (FIG. 2) of the sensor assembly are held together by thumb screws 34A and 34B (FIG. 2) which engage threaded bores 29A and 29B. The fasteners 36A–36E thread into bosses (not shown) in the inserts 38A and 38B.

The piezoelectric sensor 42 includes: (1) a piezoelectric film 46A which changes its electrical characteristics in response to changes in its strain and generates an electrical potential; and (2) a conductor 46B connected to the film which passes through the second section 32 for electrical connection to the flow measurement and control circuit 12 (FIG. 1) to which it transmits electrical signals indicating changes in the strain in the piezoelectric film 46A. The piezoelectric film 46A includes four apertures 43A–43D passing through it on opposite sides of the groove 45 to form a portion of a holding or clamping means holding the piezoelectric film 46A in place against the conduit 20 (FIG. 1 and 2).

During installation of the tubing 20, the piezoelectric film 46A is pre-stretched by the force of the tubing against the piezoelectric film 46A, the edges of which are held by the pins 41A–41D. The contact between the tubing 20 and the piezoelectric film 46A is maintained intimate by the bias from the stretching of the piezoelectric film 46A and extends over a sufficient surface area with sufficient pressure between the film and the tube 20 to supply adequate coupling for a reliable transfer of force. The coupling is adequate to cause the film to generate repeatable electrical signals in response to a range of forces transferred to it. In the preferred embodiment the area of contact between the piezoelectric film 46A and the tube 20 is ¼ square inch but can be as small as ¹⁄₁₆ square inch.

To protect the piezoelectric sensor 42, a woven fiberglass member 37 with a Teflon (trademark by Du Pont de Nemours, E. I. and Co., Wilmington, Del. 19898 for tetrafluoroethylene fluorocarbon polymers) coating on its top and bottom surfaces and fused over it to form a strong flexible member. It also includes: (1) five apertures aligned with the five apertures 33A, 33B, 33C, 33D and 33E in the housing 35 to receive the two bosses in 38A (not shown) and three bosses in 38B (not shown) that the fasteners 36A, 36B, 36C, 36D and 36E are threaded into; (2) an aperture aligned with the aperture 29A in the housing 35 to hold first section 30 and housing 35 together; and (3) four apertures 45A-45D aligned with the four smaller apertures 39A, 39B, 39C and 39D to receive four pins 41A, 41B, 41C and 41D that are also received by apertures 43A, 43B, 43C and 43D in the piezoelectric film 46A before being seated in the inserts 38A and 38B.

To receive and hold one end of the pins 41A-41D, the inserts 38A and 38B are sized to rest between the protective member 37 and the first section 30 (FIG. 2) and includes: (1) an aperture to receive fastener 34A (FIG. 2) which passes through it and engages threaded bore 29A; and (2) four holes 37A-37D in the side facing the protective member 37 to receive one end of each of the corresponding pins 41A-41D. With this arrangement, the pins 41A-41D hold the film 46A in place on opposite sides of the conduit 20 (FIG. 2) and are in turn held in place by the inserts 38A and 38B on one side and the housing 35 on the other.

In FIG. 4, there is shown an elevational sectional view of the second section 32 taken through lines 4—4 of FIG. 3 and showing the grooves 45 and 47, apertures 29A, 29B, 39D, 39E, 33B, 33C, 33D for seating pins and holding the first and second sections together. As best shown in this view, the conduits and piezoelectric sensor may be securely held in the formed solid rigid housing to receive signals from the pump. Within the groove 45 there is an enlarged portion 45E (FIG. 3) to allow expansion of conduit 20 during pulsation. The opening 47A is potted to avoid wire flexing.

In the preferred embodiment, the enlarged portion 45E of the groove 45 is a large enough area to receive the conduit 20 and piezoelectric film 46A and forms a recess with a depth approximately ¹⁄₁₆ inch. It is large enough to accommodate expansion of the conduit 20 during during pulsation and the depth should be at least the thickness of the film plus one one-thousandth of an inch.

In FIG. 5, there is shown a simplified view of the peristaltic pump assembly 16 and sensor assembly 14. As shown in this view, the sensor assembly 14 is on the inlet side of the peristaltic pump assembly 16 and in one embodiment spaced therefrom. In the preferred embodiment, the distance between a roller 21 as it contacts tube 20 and the sensor assembly 14 is 3.125 inches and should be less than 18 inches to avoid undue attenuation of the pulses imparted through the conduit and liquid from the force of pumps to the sensor assembly 14 before being sensed. Although the embodiment of FIG. 5 shows a sensing assembly 14 spaced from the rollers 21 of the pump, it is possible to locate a piezoelectric film in the pump housing positioned to sense the relaxation of the conduit 20 between compression by rollers. This will result in a change in strain within the piezoelectric film 46A. The change is strain will have a different time-amplitude characteristic when liquid is in the pump than when it has not yet reached the pump or has passed through the pump.

In FIG. 6, there is shown a block diagram of the flow measurement and control circuit 12 having a microprocessor 62 and an interface assembly shown generally at 60. In the preferred embodiment, the microprocessor 62 is a Model 64180 sold by Hitachi America, Ltd., Software Sales and Support Division, 950 Elm Avenue—No. 100, San Bruno, Calif. 94066, and includes a look-up table memory 63 as well as the normal logic components 65 forming the microprocessor central control. The software used in the preferred embodiment is attached hereto as attachment A. The look-up table memory 63 is accessed by the central control to look-up values corresponding to certain numbers of cycles of the pump 16 (FIG. 1) applied to it through the pump interface 60 through a conductor 77.

The interface 60 includes a sensor interface 70, connected to the pulse sensor assembly 14 (FIG. 1) through a conductor 46 and to the microprocessor 62 through a conductor 67, a keyboard 72 for entering data into the microprocessor 62 through a cable 72A, a pump interface 74 for transmitting start and stop signals through a cable 75 to the peristaltic pump assembly 16 (FIG. 1) in response to signals from the microprocessor 62 through a conductor 77 and a sample collector interface 76 receiving signals from the sample collector 18 (FIG. 1) on a conductor 79 and transmitting signals to the sample collector 18 through a conductor 81. The sample collector interface 76 transmit signals to the microprocessor 62 through a conductor 82 and receives signals through a conductor 84.

With this arrangement, the microprocessor receives indications of cycling of the peristaltic pump assembly 16 when the water interface reaches a predetermined location, counts those cycles and uses the count for other control functions such as moving bottles in the sample collector, stopping and reversing the pump and restarting the pump for another cycle, starting timing for the intervals between drawing samples and the like.

In the preferred embodiment, once the pumping system has determined that liquid is flowing from the amplitude of measured pulses, sensed cycles of the pump are counted during the time the amplitude of the strain pulses is above the threshold.

In FIG. 7, there is shown a block diagram of the sensor interface 70 having an input low-pass filter and pulse shaping section 71 and an output section 73. The input low-pass filter 71 is a National MF6 set to have a 45 hertz cut-off and a 0.5 volt threshold. The output section 73 shapes the input pulses to a square wave and discriminates against pulses having a time duration less than a predetermined time set by the RC circuit 73A. However, any suitable interface may be used.

Figure 8:
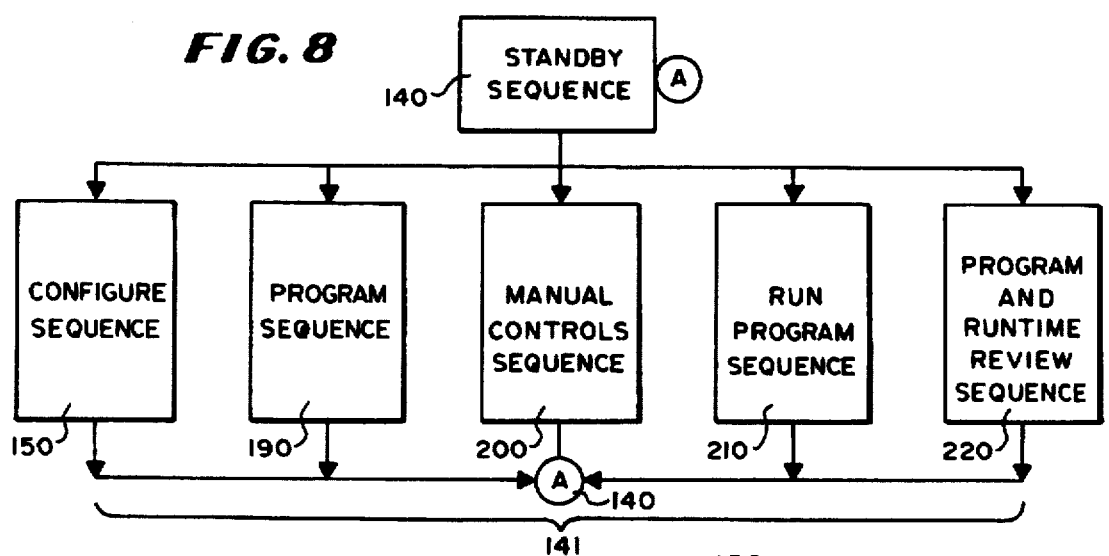
FIG. 8 is a flow diagram of a program used in the embodiment of FIG. 1.

In FIG. 8, there is shown a block diagram of the main subprograms of the program that controls the pumping system 10 (FIG. 1) including a standby mode subprogram 140 and a plurality of operating subprograms showns generally at 141. When the pumping system 10 is turned on and after completion of each of the operating subprograms shown collectively at 141, the program automatically goes to the standby mode 140. The user then enters the command to go to any of the other subprograms of the pumping system 10 (FIG. 1). The main subprograms shown in the group 141 include: (1) configure sequence 150; (2) program sequence 190; (3) manual controls 200; (4) run program 210; and (5) program and runtime review 220.

Many programs used in the operation of a pumping system are not related to the invention and are standard for equipment of this type. These programs are not described in any detail herein. However, the programs related to the invention are described in flow diagram form below and a computer printout of the code is made a part of the specification as attachment A.

Before starting the pump, the user may enter data to set up the pumping system 10 (FIG. 1) so that it will operate to the user's specific needs. If the user does not wish to change the settings from the most recent run, then he would not use these programs. This user-defined information may be entered in the configure sequence 150 and the program sequence 190. The configure sequence 150 is used to enter certain data such as bottle count and size, correct time and suction line information. Most of the data entered in the configure sequence 150 are of a type that do not change often. The program sequence 190 is used to enter data for the specifics of the sampling routine such as sample volume, frequency and distribution method.

The run program sequence 210 runs the sampling routine using the data programmed in the configure sequence 150 and program sequence 190 and the program and runtime review 220 displays the program settings and sampling routine results. The manual controls program sequence 200 sequences through steps that operate the pump and distributor in response to manually entered instructions by the operator.

Figure 9:
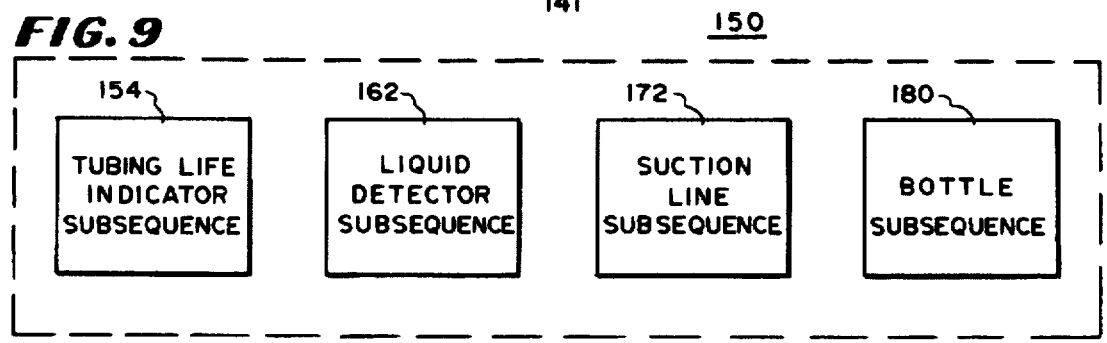
FIG. 9 is a block diagram of a portion of one of the embodiments of FIG. 8.

In FIG. 9, there is shown a block diagram of the main parts of the configure sequence 150 (FIG. 8). The parts include: (1) tubing life indicator subsequence 154; (2) liquid detector subsequence 162; (3) suction line subsequence 172; and (4) bottle subsequence 180. The subsequences together provide data points into the system for configuring the pumping system 10 (FIG. 1).

Figure 10:
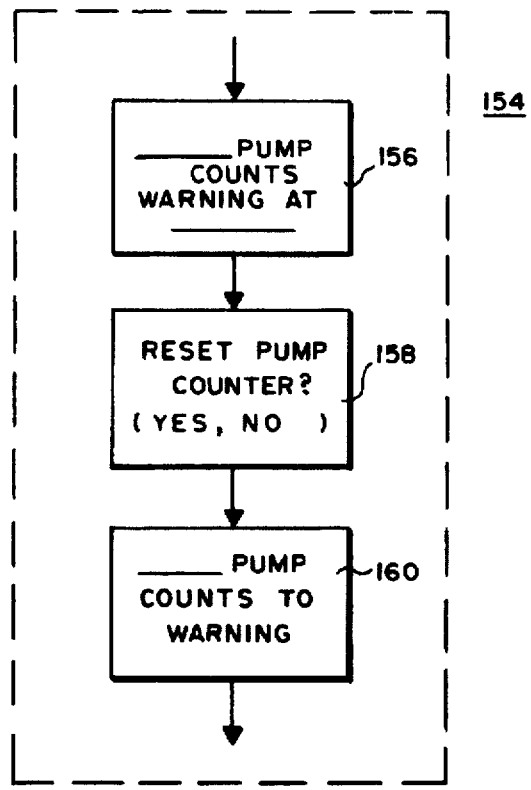
FIG. 10 is a flow diagram of a portion of the embodiment of FIG. 9.

In FIG. 10, there is shown a flow diagram of the tubing life indicator subsequence 154 (FIG. 9) of the configure sequence 150 (FIGS. 8 and 9). The tubing life indicator subsequence 154 monitors usage of the tubing 20 by keeping track of how many cycles the pump has made against the tubing 20 in any direction since its last replacement and warns the user that the tubing 20 should be replaced. Included in the tubing life indicator subsequence 154 are: (1) a pump counter subsequence at 156; (2) a reset pump counter subsequence at 158; and (3) a warning trip point subsequence at 160.

The total pump strokes (12 for each revolution of the pump) and the point at which the counter warns the user that it is time to change the tubing 20 are displayed to the user at 156. The range of pump counts for the life of the tubing 20 is usually between 50,000 and 2 million pump counts. If the tubing 20 has been replaced, the user would indicate yes in the reset pump counter subsequence 158 to reset the pump counter subsequence 156. The user-defined warning trip point is entered in subsequence 160. While the pump is pumping, the total pump counts are updated in a counter and compared to the user-defined count. When the update count exceeds the user-defined count, a warning is given.

In FIG. 11, there is shown a flow diagram of the options for the liquid detector subsequence 162 (FIG. 9) of the configure sequence 150 (FIGS. 8 and 9). The liquid detector subsequence 162 controls the liquid detector and related settings and how many times it will be used to detect liquid. The options for the liquid detector subsequence 162 include: (1) an enable/disable liquid detector subsequence 164; (2) a rinse cycle subsequence 166; (3) a manual head subsequence 168; and (4) a retry subsequence 170.

If operation of the detector is ever questionable, the user can disable it at 164. However, if the detector is disabled, the head is entered in the programming sequence 190 (FIG. 8).

To detect the liquid either in the rinse cycle or during collection of the sample, if the detector is enabled in 164, then the program requests the user to specify: (1) the number of rinse cycles in the rinse subsequence 166; (2) whether a head will be entered manually in the manual head subsequence 168; and (3) the amount of retries in the retry subsequence 170. The retry subsequence 170 controls the amount of retries for both the rinse cycles and the actual collection of sample if no liquid is detected during either process.

In FIG. 12, there is shown a flow diagram of the suction line subsequence 172 (FIG. 9) of the configure sequence 150 (FIGS. 8 and 9). The suction line subsequence 172 is used gather information concerning the suction line, generates the look-up tables and sets the number of post-purge counts. The subsequences in this program are: (1) the inner diameter subsequence 174; (2) the material subsequence 176; and (3) the length subsequence 178.

In the preferred embodiment, the inner diameter of the suction line entered in the subsequence 174 is entered in inches such as one-quarter inch or three-eighths of an inch, the choice of suction line entered in the material subsequence 176 is either vinyl or Teflon and the length of the suction line entered in the length subsequence 178 can be between three and ninety-nine feet.

In FIG. 13, there is shown a flow diagram of the bottle subsequence 180 (FIG. 9) of the configure sequence 150 (FIGS. 8 and 9). The bottle subsequence 180 is used to set maximum sampling volumes and provide information to the distributor movement routine.

Two of the subsequences included in the bottle subsequence 180 are bottle number subsequence 182 and bottle volume subsequence 184. The bottle number subsequence 180 is used to enter the amount of bottles in the base and the bottle volume subsequence 184 is used to enter the maximum volume of liquid to be inserted into each bottle.

In FIG. 14, there is shown a flow diagram of portions of the program sequence 190 (FIG. 8). The program sequence 190 is for entering specifics of a sampling routine which include: (1) the bottles per sample subsequence 192; (2) the sample volume subsequence 194; and (3) the head subsequence at 196. The number of bottles per sample is entered in the sample subsequence 192 and the amount of sample to be distributed into each bottle is entered in the sample volume subsequence 194.

To ensure a more accurate calculation of the pump count maximum or if the liquid detector was disabled, the suction head is entered in the head subsequence 196. The suction head is used if the liquid detector was disabled at 164 in the liquid detector subsequence 162 or the user indicated in the head subsequence 168 that a head would be manually entered (FIG. 11). In the preferred embodiment, the user can enter a minimum volume of sample of 10 milliliters and a minimum suction head of one foot.

Figure 15:
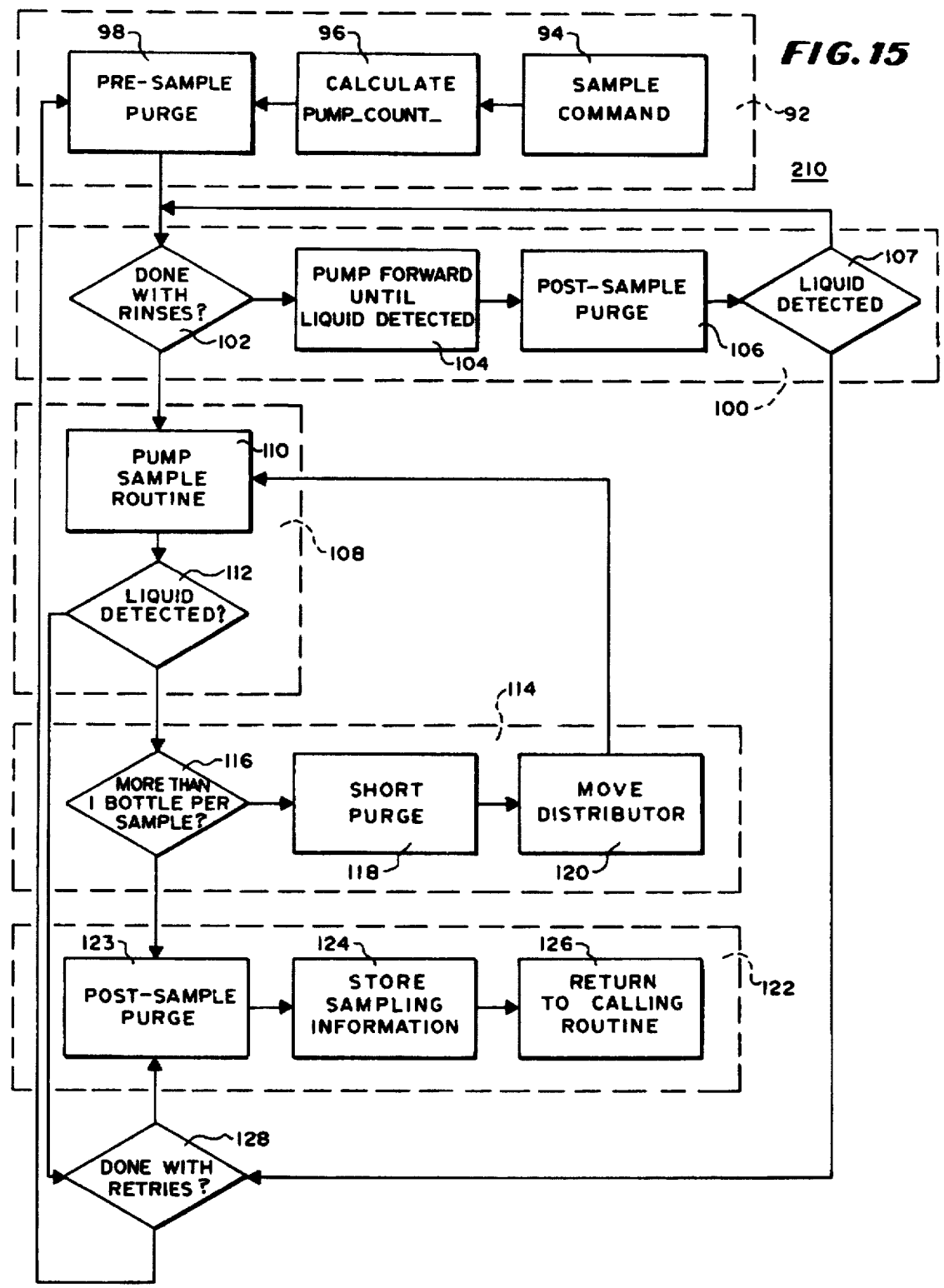
FIG. 15 is a flow diagram of a portion of still another embodiment the program of FIG. 8.

In FIG. 15, there is shown a flow diagram of a portion of the run program sequence 210 for drawing and distributing a sample in accordance with an embodiment of the invention. The run program sequence 210 includes: (1) the series of steps 92 relating to starting the pump; (2) the rinse routine 100; (3) the series of steps 108 relating to drawing a sample; (4) the series of steps 114 relating to distributing the sample; (5) the series of steps 122 relating to storage of the sampling information; and (6) the step 128 of retrying a rinse routine or pump sample routine.

The series of steps 92 relating to starting the pump include the step 94 of receiving the sample command, the step 96 of calculating the maximum pump count and the pre-sample purge step 98. After the sample command 94 has been received, a maximum pump count is calculated based on the head entered in the head subsequence 196 (FIG. 14) or the head from the previous sample if no head was entered. Only one value for the head is used to calculate the maximum pump counts and is used throughout the program segment. The pre-sample purge command 98 is then performed to clear the strainer of any debris which may have collected since the last sample was taken.

After the pre-sample purge is completed, the rinse routine 100 is activated which includes the step 102 to determine if a rinse should be performed or if a second or third rinse should occur. Rinse routines have already been preprogrammed by the user in the rinse subsequence 166 (FIG. 11). If a rinse is programmed, the liquid is pumped forward in the step 104 until a predetermined amount of liquid is detected in step 107 and the liquid is purged in the step 106.

If the predetermined amount of rinse liquid is detected as having reached its destination, the rinse routine 100 is begun again as indicated at 102. If another rinse routine is remaining, the liquid is pumped forward at 104 and the remaining steps of the rinse routine are carried out. The rinse routine 100 is repeated until there are no further rinses. When the rinses are complete, the series of steps 108 relating to drawing a sample continues with the pump sample routine 110 and the step 112 of detecting the liquid.

If no liquid was detected during the rinse routine 100 in the step 107 or the step 112 of the series of steps 108, the program in the step 128 accesses the retry subsequence 170 of the liquid detector subsequence 162 (FIG. 11) to find out if it should retry pumping sample before shutting down. If the user entered any retries, and the total amount of retries has not been met, the program returns to the pre-sample purge 98 and starts the rinse routine 100.

If all of the retries have been made or if no retries were programmed, the controller performs a post sample purge at 123, stores the sampling information at 124 and returns to the calling routine at 126 of the steps 122.

If a rinse routine 100 was not programmed, the steps 104, 106 and 107 are skipped and the program goes directly to drawing a sample at 110 and determines if liquid is detected at 112. The pump sample routine 110 is the actual process of drawing and measuring the sample and will be later described in more detail.

When it is indicated at 112 that liquid was detected, the series of steps 114 relating to distributing a sample is performed. The first step of the series of steps 114 is the step 116 of determining if sample is to be inputted into one or more bottles. If only one bottle will be filled, a user-defined amount of sample is then emptied into the bottle, a post sample purge is performed at 123, the sampling information is stored at 124, and the program returns to the calling routine at 126 in the series of steps 122.

If there is more than one bottle to be filled, a short purge 118 is made to back the liquid up so that it can detect a second user-defined amount of sample and the the distributor is moved to the next sample bottle at 120.

The program segment 210 then returns to the pump sample routine 110 until data is received at 112 that the user-defined amount of liquid is detected. The program checks whether there is more than one bottle left to fill at 116 and then empties the sample into a sample bottle. If more sample is needed, the remaining steps, 118 of purging the sample and 120 of moving the distributor to the next bottle are repeated again. The steps of emptying the sample into the bottle at 116, purging the liquid at 118 and moving the distributor at 120 are repeated until it is indicated at 116 that no more sample will be distributed. When no more sample is needed, a post sample purge is performed at 123, the sampling information is stored at 124, and the program returns to the calling routine at 126 in the series of steps 122.

Figure 16:
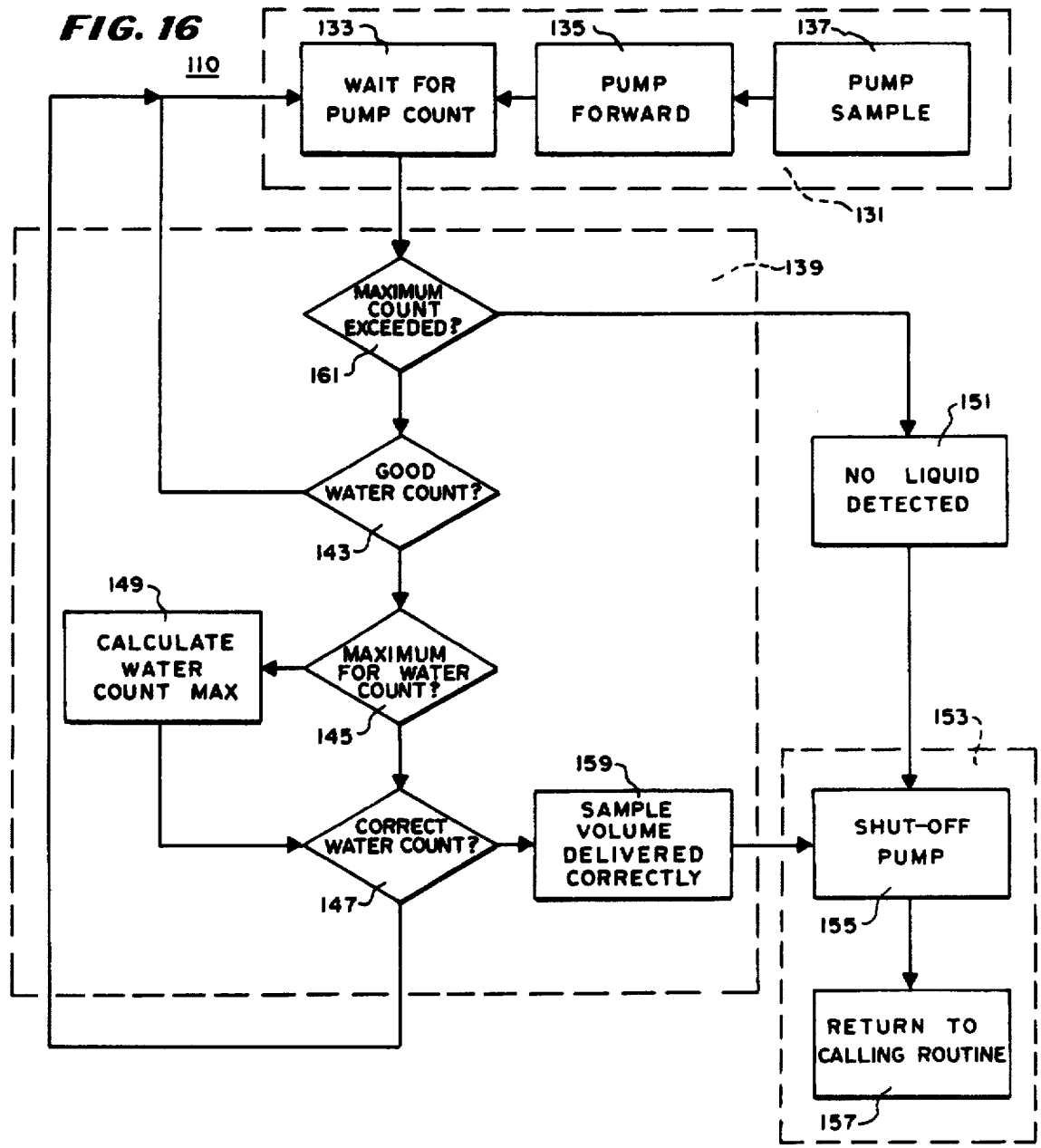
FIG. 16 is a flow diagram of a portion of the program segment of FIG. 15.

In FIG. 16, there is shown a flow diagram of the pump sample routine 110 of the program segment 210 (FIG. 15) for drawing and distributing a sample. This routine is the actual pumping of the sample to collect a predetermined amount of liquid in a sample bottle. The pump sample routine 110 includes: (1) the series of steps 131 relating to the beginning stages of pumping; (2) the series of steps 139 related to obtaining the water count; (3) the step 151 of saving information that no liquid was detected; and (4) the series of steps 153 of stopping the pump.

In the series of steps 131, a pump sample command is received at 137 and the sample is pumped upstream through the tubing 20 (FIGS. 1, 2 and 5). The sample is then continually pumped and the program waits for a pump count change at 133. The maximum pump count was predetermined based on the head of the previous sample or measured by the user and entered into the program before the user began the pump (not shown) in the configure sequence 150 (FIG. 8).

The program 110 then goes through a series of steps at 139 starting with determining if the maximum pump count has been exceeded in the step 161. If the maximum pump count has been exceeded, the program will save the information indicating that no liquid was detected at 151 and proceed to the series of steps 153 of stopping the pump. During shutdown of the pump, the program shuts the pump off at 155 and returns to the calling routine at 157.

If the maximum pump count has not been exceeded at 161, it is then determined whether a good water count was found at 143. The program determines if a water count is received so near to the beginning of a sample drawing run as to indicate an error. This can occur in the first few cycles such as for example four cycles of the pump. After a predetermined number of cycles of the pump, this type of error tends not to occur. In the preferred embodiment, the pump must have counted at least 50 counts before the count is considered good. If it was not a good water count, the program: (1) returns to waiting for the pump count at 133; and (2) maintains in memory the amount of water counts already received and adds a new water count to the previously received water counts.

If it was a good water count, it is then determined if a new maximum amount of water counts should be calculated at 145. If a new maximum should be made, the program calculates a new maximum water count at 149, using the head from the previous sample or the head defined by the user in the head subsequence 196 (FIG. 14), and then decides at 147 if the sample water count is the correct amount. If not enough sample was pumped, the program returns to the wait for the pump count at 133 and pumps more liquid until it has pumped a predetermined amount of pump counts and continues with the series of steps 139 starting at 161 to determine if the maximum count was exceeded. If the pump did receive a correct water count, it is recorded in memory at 159 that the sample volume was delivered correctly and proceeds with the series of steps 153 of shutting down the pump at 155 and returning to the calling routine at 157.

If it is not necessary to calculate the maximum water count, then the program skips the step 149 and determines at this point if it is a correct water count at 147, records that the sample volume was delivered correctly at 159 and proceeds with the series of steps 153 of shutting off the pump at 155 and returning to the calling routines at 157.

When the program returns to the calling routine at 157, the memory is accessed to find out if the liquid was detected at 112 (FIG. 15) and if it was not, the program would advance to the program at 128 to access 170 of the options for the liquid detector control 162 (FIG. 9) of the configure sequence 150 to find out if it should retry pumping sample before shutting down. If the user entered any retries, and the total amount of retries has not been met, then the program returns to purging the pre-sample at 98 and continuing with the rinse routine 100 (FIG. 15).

In FIG. 17, there is shown a flow diagram of the program and run review sequence 220 (FIG. 8). The program and run review sequence 220 is used to check program setting or sampling routine results. The subsequences included are the pump tubing warning subsequence 222 and the sample information for the last sample routine subsequence 223.

Each time the pump count maximum for replacing the tubing is exceeded, the pump tubing warning message at 222 is displayed. The threshold for the pump count maximum has been user-defined in the tubing life indicator control 154 at 156 (FIG. 10) before beginning the pump. If the user does not enter a new threshold, the threshold from the previous sampling process will be used.

After each sample gathering process, certain information is stored in memory for future use at 223. Included are: (1) if the sample process was performed and no liquid was detected at 224; (2) the time and date at 226; and (3) the number of pump counts before liquid was detected at 228 and the amount of time for the entire pump cycle. The number of counts before liquid was detected at 228 is used to calculate the head at 149 (FIG. 16).

In FIG. 18, there is shown a block diagram of another embodiment of tubing life indicator circuit 154A for providing a signal after a predetermined number of strokes of roller against the tube 20 (FIGS. 1, 2 and 5) in the peristaltic pump assembly 16 (FIG. 1), having the cycle signal generator 11, a counter 240, a switch 246, a manually resettable switch 242 and a warning light 252. The counter 240 is directly connected to the conductor 13 to receive all counts regardless of direction and having an output set at a predetermined number of counts connected to the resettable switch 242 to actuate the switch at the predetermined number of counts and thus energize the warning light to which it is connected.

With this arrangement, the operator may set the counter 240 at a count that indicates the tube 20 (FIGS. 1, 2 and 5) should be replaced. When the number of pulses from the cycle signal generator 11 reaches the preset number, the counter 240 supplies a signal to the resettable switch 242 which applies a signal from the source of voltage 254 to the warning light 252. The resettable switch 242 can be manaully reset when the tube is changed and it resets the counter 240 and disconnects the power 254 from the warning light 252.

To permit a hardware determination of the direction of rotation, the switch 246 receives pulses from the conductor 13 and a direction signal from the cycle signal generator 11 to switch from one of the two output conductors 248 or 250 to the other so that pulses representing the number cycles in each direction can be determined. This function can also be performed in software.

From the above description, it can be understood that the pumping system of this invention has several advantages, such as for example: (1) it more precisely meters the amount of liquid because it is based on pulsations and pump cycles which react to the head of pressure; (2) measurement is made using a criteria which is not altered by splashing or surging of the water or the light transmission characteristics of an optical path or the capacitance or other noise affects that has caused difficulties with other types of sensors; and (3) the metering criteria is partly determined by a statistical base to compensate more readily for variations from sample to sample.

Although a preferred embodiment has been described with some particularity, many modifications and variations of the preferred embodiment can be made without deviating from the invention. Therefore, it is to be understood that, within the scope of the appended claims, the invention may be practiced other than as specifically described.

What is claimed is:

1. A method of making a sensor for detecting a liquid in a flexible conduit comprising the steps of:

providing a flexible conduit means;

forming a loop of the flexible conduit means said loop having two legs, and positioning said loop in cooperation with a peristaltic pump;

mounting said legs in a fixture wherein a strain-sensitive film in the fixture is positioned adjacent and in contact with one of said legs to sense pressure within the flexible conduit means; and providing electrical connections to the strain-sensitive film adapted to sense periodic strains whereby pulses of pressure transmitted through the flexible conduit means may be detected.

2. A method of making a sensor according to claim 1 in which the step of mounting a flexible conduit means includes the step of mounting a flexible tube and a strain-sensitive film in the fixture wherein the strain-sensitive film and the flexible tube are supported at a location adjacent to a conduit support means whereby at least a portion of the strain-sensitive film is in contact with the conduit when the fixture and conduit are assembled.

3. A method of making a sensor according to claim 2 including the step of permitting:

sufficient expansion of the conduit to create strain of an amplitude to permit discrimination of signal from noise wherein said strain-sensitive film is partly stretched in the fixture whereby liquid pumped through the conduit may be detected.

4. A method of making a sensor according to claim 1 including the step of permitting sufficient expansion of the conduit in an opening having a depth of at least the thickness of the conduit plus one-thousandth of an inch.

5. A method of making a sensor according to claim 1 wherein said strain-sensitive film is pre-stretched by the conduit during installation of the conduit into a means for receiving said conduit.

6. A method of making a sensor according to claim 1 wherein after installation said strain-sensitive film has contact with the conduit of at least one-sixteenth of a square inch.

7. A method of making a sensor according to claim 1 including the step of mounting the fixture and a pump at a distance from each other sufficiently close to detect the difference in amplitude of strain when liquid reaches a predetermined point from amplitude before it reaches the predetermined point.

8. A method of making a sensor according to claim 1 in which the strain sensitive film is mounted at a distance no greater than 18 inches from a pump.

9. A method of making a sensor according to claim 1 in which the strain-sensitive film is mounted on the inlet side of a pump.

10. A method of making a sensor according to claim 1 in which the electrical connections to the strain-sensitive film are connected to a programmable computer.

11. A method of making a sensor according to claim 1 including the step of connecting the strain-sensitive film to a programmable computer means for predicting the number of force pulses transmitted through the flexible conduit means to the sensor before sensing the liquid; said programmable computer means having a statistical database.

12. A method of making a sensor according to claim 1 wherein a programmable computer means is programmed to determine which pulses are sensed; said programmable computer means being programmed to count slugs of liquid only when followed by a flow of liquid.

13. A method of making a sensor according to claim 1 including the step of determining when a predetermined volume of liquid has been pumped to a container; counting pulses applied to said electrical connections, and reading from a look-up table the volume of liquid deposited corresponding to said counted pulses.

* * * * *